(12) United States Patent
Kurz et al.

(10) Patent No.: US 8,191,554 B2
(45) Date of Patent: Jun. 5, 2012

(54) NIPPLE COVERING SYSTEM

(75) Inventors: Daniel R. Kurz, Sunnyvale, CA (US); Lynn Seely, Burlingame, CA (US)

(73) Assignee: Dr. Susan Love Research Foundation, Santa Monica, CA (US)

( * ) Notice: Subject to any disclaimer, the term of this patent is extended or adjusted under 35 U.S.C. 154(b) by 0 days.

(21) Appl. No.: 13/083,442

(22) Filed: Apr. 8, 2011

(65) Prior Publication Data

US 2011/0184355 A1    Jul. 28, 2011

Related U.S. Application Data

(63) Continuation of application No. 12/368,257, filed on Feb. 9, 2009, now Pat. No. 7,921,851, which is a continuation of application No. 11/291,738, filed on Dec. 1, 2005, now Pat. No. 7,487,779, which is a continuation of application No. 09/793,110, filed on Feb. 27, 2001, now abandoned.

(51) Int. Cl.
*A61F 13/00* (2006.01)
(52) U.S. Cl. ........................................ 128/889; 128/890
(58) Field of Classification Search .......... 128/887–890; 602/41–48, 52–58
See application file for complete search history.

(56) References Cited

U.S. PATENT DOCUMENTS

| | | | |
|---|---|---|---|
| 65,978 A | 6/1867 | Wilder et al. | |
| 3,229,691 A * | 1/1966 | Crowe, Jr. | ............ 602/1 |
| 3,782,377 A | 1/1974 | Rychlik | |
| 3,786,801 A | 1/1974 | Sartorius | |
| 3,840,012 A | 10/1974 | Rushton, Jr. | |
| 3,867,517 A | 2/1975 | Ling | |
| 4,036,945 A | 7/1977 | Haber | |
| 4,195,639 A | 4/1980 | Lee | |

(Continued)

FOREIGN PATENT DOCUMENTS

DE    3907007    9/1990

(Continued)

OTHER PUBLICATIONS

Bobo et al., "Findings from 752081 Clinical Breast Examinations Reported to a National Screening Program From 1995 Through 1998", Journal of the National Cancer Institue, 2002, vol. 92, Issue 12, pp. 971-976.

(Continued)

*Primary Examiner* — Michael A. Brown
(74) *Attorney, Agent, or Firm* — Knobbe, Martens, Olson & Bear, LLP

(57) ABSTRACT

One aspect of the present invention relates to a covering member for a protruding portion of a patient's body. This cover is flexible and collapsible so that it conforms to the shape of the encased portion of the body. This prevents the cover from being noticed while it is worn under clothing. The cover can contain a medicament or agent for pretreating a portion of the body before an examination or procedure. When the cover is used to apply a topical anesthetic to a portion of the body for a recommended period of time prior to the procedure or examination commencing, the amount of discomfort experienced by the patient can be significantly reduced compared to the amount experienced by the patient who has the anesthetic applied for just a few moments before the procedure begins. Alternatively, the cover can be used to hold a medicament or agent on the intended portion of the body in order to heal a wound or cure a condition such as a skin rash or the like.

17 Claims, 4 Drawing Sheets

U.S. PATENT DOCUMENTS

| | | | |
|---|---|---|---|
| 4,302,438 | A | 11/1981 | Zech |
| 4,311,688 | A | 1/1982 | Burchiel et al. |
| 4,333,471 | A | 6/1982 | Nakai |
| 4,376,110 | A | 3/1983 | David et al. |
| 4,640,288 | A | 2/1987 | Hattori |
| 4,667,666 | A | 5/1987 | Fryslie |
| 4,732,864 | A | 3/1988 | Tolman |
| 4,754,750 | A | 7/1988 | Imonti |
| 4,870,977 | A | 10/1989 | Imonti |
| 4,917,112 | A | 4/1990 | Kait |
| 5,032,103 | A | 7/1991 | Larsson |
| 5,230,350 | A * | 7/1993 | Fentress ............... 128/846 |
| 5,348,860 | A | 9/1994 | Shamsuddin |
| 5,416,025 | A | 5/1995 | Krepinsky et al. |
| 5,627,034 | A | 5/1997 | Gould et al. |
| 5,740,550 | A * | 4/1998 | Yavitz .................... 2/15 |
| 5,743,272 | A | 4/1998 | Kocher, Jr. |
| 5,798,266 | A | 8/1998 | Quay et al. |
| 5,910,125 | A | 6/1999 | Cummings et al. |
| 6,005,159 | A * | 12/1999 | Spier ................... 602/42 |
| 6,036,029 | A | 3/2000 | Gommel et al. |
| 6,063,029 | A | 5/2000 | Saita et al. |
| 6,093,160 | A * | 7/2000 | Augustine et al. ........... 602/2 |
| 6,096,943 | A | 8/2000 | Maiwald |
| 6,168,779 | B1 | 1/2001 | Barsky et al. |
| 6,187,591 | B1 | 2/2001 | Krepinsky et al. |
| 6,221,622 | B1 | 4/2001 | Love et al. |
| 6,287,521 | B1 | 9/2001 | Quay et al. |
| 6,570,050 | B2 | 5/2003 | Augustine et al. |
| 6,642,009 | B2 | 11/2003 | Hung |
| 7,487,779 | B2 | 2/2009 | Kurz et al. |
| 7,879,614 | B2 | 2/2011 | Krepinsky et al. |
| 7,921,851 | B2 | 4/2011 | Kurz et al. |
| 2001/0039015 | A1 | 11/2001 | Sauter |
| 2002/0117169 | A1 | 8/2002 | Kurz et al. |
| 2006/0030787 | A1 | 2/2006 | Quay |
| 2006/0246415 | A1 | 11/2006 | Krepinsky et al. |
| 2011/0124110 | A1 | 5/2011 | Krepinsky et al. |

FOREIGN PATENT DOCUMENTS

| | | |
|---|---|---|
| EP | 1377337 | 4/2007 |
| EP | 1554584 | 5/2008 |
| FR | 792353 | 12/1935 |
| GB | 2150028 | 6/1985 |
| WO | WO 95/14927 | 6/1995 |
| WO | WO 02/068038 | 9/2002 |
| WO | WO 2004/034059 | 4/2004 |
| WO | WO 2008/141318 | 11/2008 |

OTHER PUBLICATIONS

Borg et al., "BRCA1 1675delA and 1135insA Account for One Thrid of Norweigan Familial Breast-Ovarian Cancer and Are Associated with Later Disease Onset for Less Frequent Mutations", Disease Marketers, Issue 15, pp. 79-84.

Bradwell et al., "Developments in Antibody Imaging" in Monoclonal antibodies for cancer detection and therapy, Academic Press, 1985, pp. 65-85.

Breen et al., "Changes in the Use of Screening Mammography: Evidence from the 1987 and 1990 National Health Interview Surveys", American Journal of Public Health, 1994, vol. 84, Issue 1, pp. 62-67.

Buckley et al., "Ann efficient method for labeling antibodies with In", FEBS Lett., 1984, vol. 166, Issue 1, pp. 202-204.

David et al., "Protein Iodination with Solid State Lactoperoxidase", Biochemistry, 1974, vol. 12, Issue 5, pp. 1014-1021.

Ernster et al., "Incidence of and Treatment for Ductal Carcinoma in Situ of the Breast", J. Am. Med. Assoc., 1996, vol. 275, pp. 913-918.

Feuer et al, "How Much of the Recent Rise in Breast Cancer Incidence Can be Explained by Increases in Mammography Utilization?", American Journal of Epidemiology, 1992, vol. 136, Issue 12, pp. 1423-1436.

Gotzche et al, Is screening for breast cancer with mammography justifiable?, The Lancet, 2000, vol. 355, pp. 129-134.

Greenlee et al., Cancer Statistics, 2001, CA: A Cancer Journal for Clinicians, 2001, vol. 51, pp. 15-36.

Greenwood et al., The Preparation of 131I-Labeled Human Growth Hormone of High Specific Radioactivity, Biochem, 1963, vol. 89, pp. 114-123.

Hayes, D.F., Tumor markers for breast cancer, Anals of Oncology, 1993, vol. 4, pp. 807-819.

Hnatowich et al., The Preparation of DTPA-Couled Antibodies Radiolabeled with Metallic Radionuclides: an Improved Method, Journal of Immunological Methods, 1983, vol. 65, pp. 147-157.

Holmberg et al., Breast cancer mortality in relations to self-reported use of breast self-examination. A cohort study of 450,000 women, Breast Cancer Research and Treatment, 1997, vol. 43, pp. 137-140.

Hunter et al., Preparation of Iodine-131 Labelled Human Growth Hormone of High Specific Activity, Nature, 1962, vol. 194, pp. 495-496.

International Search Report Dated Apr. 1, 2004 for PCT/CA03/001553 filed Oct. 9, 2003.

International Search Report dated Aug. 6, 2008 for PCT Application No. PCT/US08/63545 filed May 13, 2008.

International Search Report dated Jul. 16, 2002 for PCT Application No. PCT/US0205202 filed Feb. 22, 2002.

Katagiri et al., High proportion of missense mutations of the BRCA1 and BRCA2 genes in Japanese breast cancer families, J. Hum. Genet., 1998, vol. 43, pp. 42-48.

Kelsey et al., Epidemiology and Prevention of Breast Cancer, Annu. Rev. Public Health, 1996, vol. 17, pp. 47-67.

Krepinsky et al., From T-antigen to plasmalogen-derived aldehydes: The identification of a marker of colorectal cancer in human rectal mucous, Can. J. Chem., 2003, vol. 81, pp. 109-117.

Kuhl et al., Healthy Premenopausal Breast Parenchymain Dynamic Contrast-enhanced MR Imaging of the Breat: Normal Contrast medium Enhancement and Cyclical-Phase Dependency, Radiology, 1997, vol. 203, pp. 137-144.

Lee et al., Association of Abnormal Nipple Aspirate Cytology and Mammographic Pattern and Density, Cancer Epidemiology, Biomarkers & Prevention, 1994, vol. 3, pp. 33-36.

Lee et al., The Association of Deitary Fat with Ability to Obtain Breast Fluid by Nipple Aspiration, Cancer Epidemiology, Biomarkers & Prevention, 1992, vol. 1, pp. 277-280.

Love et al., Breast-duct endoscopy to study stages of cancerous breast disease, The Lancet, 1996, vol. 348, pp. 997-999.

Mandel et al., Reducing Mortality From Colorectal Cancer by Screening for Fecal Occult Blood, New England Journal of Medicine, 1993, vol. 328, Issue 19, pp. 1365-1371.

Marchalonis, J.J., An Enzymic Method for the Trace Iodination of Immunoglobulins and other Proteins, Biochem J., 1969, vol. 113, pp. 299-305.

Mausner et al., Epidemiology: An Introductory Text, W.B. Saunders, 1974, pp. 242-243, St. Louis, USA.

Merchant et al., P Magnetic resonance phospholipid profiles of neoplastic human breast tissues, Brit. J. Cancers, 1991, vol. 63, pp. 693-698.

Morrison et al., Use of Lactoperoxide Catalyzed Iodination in Immunochemical Studies, Immunochemistry, 1971, vol. 8, pp. 289-297.

Najafi et al., Coupling Antibody with DTP A—An Alternative to the Cyclic Anhydride, Int. J. Appl. Radiat. Isot., 1984, vol. 35, Issue 6, pp. 554-557.

Olsen et al., Cochrane review on screening for breast cancer with mammography, The Lancet, 2001, vol. 358, pp. 1340-1342.

Olsen et al., Screening for breast cancer with mammography (Review), Cochrane Library, 2001, Issue 4, Oxford.

Petrakis et al., Association of Breast fluid coloration with age, ethnicity, and cigarette smoking, Breast Cancer Research and Treatment, 1988, vol. 11, pp. 255-262.

Petrakis et al., Birthplace and Yield of Nipple Aspirate Fluid in Chinese Women, Cancer Epidemiology Biomarkers & Prevention, 1998, vol. 7, pp. 835-839.

Petrakis, Nicholas L., Nipple Aspirate Fluid in Epidemiologic Studies of Breast Disease, Epidemiologic Reviews, 1993, vol. 15, Issue 1, pp. 188-195.

Petrakis, Nicholas L., Physiologic, biochemical, and cytologic aspects of nipple aspirate fluid, Breast Cancer Research and Treatment, 1986, vol. 8, pp. 7-19.

Petrakis, Nicholas L., Studies on the Epidemiology and Natural History of Benign Breast Disease and Breast Cancer Using Nipple Aspirate Fluid, Cancer Epidemiology, Biomarkers & Prevention, 1993, vol. 2, pp. 3-10.

Ransohoff et al., Screening for Colorectal Cancer, New England Journal of Medicine, 1991, vol. 352, Issue 1, pp. 37-41.

Rhodes et al., 99mTc-Labeling and Acceptance Testing of Radio labeled Antibodies and Antibody Fragments, Burchiel SW, Rhodes BA, Friedman BE Tumor Imaging: The radioimmunochemical detection of cancer, 1982, pp. 111-123, Masson.

Ringash, Jolie, Preventative health care, 2001 update: screening mammography among women aged 40—40 years at average risk of breast cancer, J. Can. Med. Assoc., 2001, vol. 164, pp. 469-476.

Robins et al., The structure of Schiff reagent aldehyde adducts and the mechanism of the Schiff reaction as determined by nuclear magnetic resonance spectroscopy, Can. J. Chem., 1980, vol. 58, pp. 339-347.

Runge et al., Paramagnetic NMR Contrast Agents Development and Evaluation, Invest. Radiol., 1984, vol. 19, pp. 408-415.

Santarosa et al., Low Incidence of BRCA1 Mutations Among Italian Families With Breast and Ovarian Cancer, Int. J. Cancer, 1998, vol. 78, pp. 581-586.

Sartorius, Otto, Breast fluid cells help in early cancer detection, Am. Med. Assoc., 1973, vol. 224, pp. 823-827.

Sauter et al., Biologic Markers of Risk in Nipple Aspirate Fluid Are Associated With Tumour Size, British Journal of Cancer, 1981, vol. 7, Issue 1999, pp. 1222-1227.

Sauter et al., Nipple aspirate fluid: a promising non-invasive method to identify cellular markers of breast cancer risk, British Journal of Cancer, 1997, vol. 76, Issue 4, pp. 494-501.

Schaefer et al., In Vivo Nuclear Mangetic Resonance Imaging of Myocardial Perfusion Using the Paramagnetic Contrast Agent Manganese Gluconate, JACC, 1989, vol. 14, Issue 2, pp. 472-480.

Self-Reported Use of Mammography and Insurance Status Among Women Aged greater than or equal to 40 Year-United States, 1991-1992 and 1996-1997, Morbidity and Mortality Weekly Report, 1998, vol. 47, pp. 825-830.

Shao et al., Nipple Aspiration in Diagnosis of Breast Cancer, Seminars in Surgical Oncology, 2001, vol. 20, pp. 175-180.

Teh et al., The Role of Ultrasound in Breast Cancer Screening. A Consensus Statement by the European Group for Breast Cancer Screening, European Journal of Cancer, 1998, vol. 34, Issue 4, pp. 449-450.

Wagner et al., Denaturing High-Performance Liquid Chromatography Detects Reliably BRCA1 and BRCA2 Mutations, Genomics, 1999, vol. 62, pp. 369-376.

Wesbey et al., Paramagnetic Pharmaceuticalsfor Magnetic Resonance Imaging, Physiological Chemistry and Physics and Medical NMR, 1984, vol. 16, pp. 145-155.

Wolf et al., Contrast Enhancement in Biomedical NMR, Physiological Chemistry and Physics and Medical NMR, 1984, vol. 16, pp. 93-95.

Wrensch et al., Breast Cancer Incidence in Women with Abnormal Cytology in Nipple Aspirates of Breast Fluid, American Journal of Epidemiology, 1992, vol. 135, Issue 2, pp. 130-141.

Wrensch et al., Breast Cancer Risk Associated with Abnormal Cytology in Nipple Aspirates of Breast Fluid and Prior History of Breast Biopsy, American Journal of Epidemiology, 1993, vol. 137, Issue 8, pp. 93-95.

* cited by examiner

NIPPLE COVERING SYSTEM

CROSS-REFERENCE TO RELATED APPLICATIONS

This application is a continuation of U.S. patent application Ser. No. 12/368,257, filed Feb. 9, 2009, which is a continuation of U.S. patent application Ser. No. 11/291,738, filed Dec. 1, 2005, now U.S. Pat. No. 7,487,779, issued Feb. 10, 2009, which is a continuation of U.S. patent application Ser. No. 09/793,110, filed Feb. 27, 2001, now abandoned, all of which are hereby incorporated by reference herein in their entireties.

BACKGROUND

1. Field of the Inventions

The present invention relates to a device for covering and applying a medicament to a protruding portion of a mammalian body. More specifically, the present invention relates to a flexible, continuous covering apparatus that surrounds the protruding body portion in order to protect it and/or retain a medical agent on it before or after an operation or other medical procedure has been performed.

2. Description of the Related Art

Certain medical procedures require that an agent, such as a medicament, be topically applied to, and maintained on, a portion of a patient's body. The need for the agent can arise before or after the medical procedures have been performed. These procedures can comprise patient examinations, minimally invasive diagnostic operations, exploratory operations and invasive therapeutic operations. The patient examinations may include the step of positioning a medical device, such as a probe, scope or catheter, within a body passageway to perform an examination or retrieve material from within the passageway or a related body cavity, such as a duct.

Topical anesthetics are an example of one class of medicaments that may be applied to the portion of the body hours before and/or after the intended procedure is performed. For example, topical anesthetics can prepare the body portion to receive a medical device that will be positioned within a body opening or incision during the procedure. A composition including an anesthetic and another active agent may also be used. In the situation where the composition is applied to a breast to prepare it for ductal access, a dekeratinizing agent and/or a ductal orifice dilating agent such as capsicum may be used. Agents applied post procedure might include topical antibiotics or well-known wound healing agents.

When the anesthetic is applied before the procedure, a cover, such as a bandage, is normally positioned over the anesthetic to prevent it from being prematurely wiped off. However, conventional covers do not offer the patient an effective option for covering the anesthetic for an hour or any other extended period of time that is sufficient to prepare (numb) the body portion. Instead, these covers lay like a flat drape, are normally ineffective and are uncomfortable to wear, especially when the patient is active between the time the anesthetic is applied and the procedure is performed. Hence, the patient may only wear the cover and the anesthetic for a short time before the procedure begins. Unfortunately, when this occurs, the amount of discomfort experienced by the patient during the procedure may be significantly increased.

Alternatively, the bandages can be wrapped circumferentially around the portion of the body being treated like an open ended cylinder if the treated portion is part of or all of a protruding body member. However, these bandages do not cover, encapsulate and isolate the portion of the body from its normal environment. Examples of the protruding body portions that do not form effective seals with conventional bandages include, but are not limited to, nipples, fingers, toes, noses and pediatric penises.

When either of the conventional bandages is used on one of these protruding body portions, they cannot effectively cover and enclose the applied agent so that it does not leak out. Instead, the applied medicament may leak out from under the bandage and onto other parts of the patient including her clothing. This can result in less than a preferred amount of the agent remaining on the protruding body portion for the prescribed period of time. If enough leaks out from under the bandage, the overall effectiveness of the agent will be significantly reduced and the procedure may have to be postponed. If the procedure is not postponed, as discussed above, the patient may experience an unnecessary amount of pain and discomfort. When either circumstance occurs, the patient and the healthcare facility can become frustrated. If excessive amounts of the agent are applied in anticipation of some of it leaking out from under the bandage, the added amount may adversely effect the adhesive portion of the bandage and prevent any portion of it from adhering to the patient. If this occurs, the amount of the agent that will leak out from under the bandage will be excessive.

Other problems may also occur with the use of flat bandages. For example, it could be very embarrassing if the applied agent leaks out from under the bandage and stains the patient's shirt, pants, etc. The embarrassment may be enhanced depending on the location of the stain. Additionally, the cost of cleaning or replacing the garment that has been stained can be significant. These additional costs may frustrate the patient and possibly discourage her from having the same procedure or examination performed again. Moreover, problems and embarrassment can result if the stains cause other people to question their origin and learn about the procedure that the patient is about to undergo.

Covers for specific protruding body portions are well known. One such type of cover includes nipple covers for lactating nipples that permit expelled fluid to dry on the nipple. Examples of these covers are disclosed in U.S. Pat. No. 3,840,012, to Rushton, Jr., U.S. Pat. No. 5,032,103, to Larsson and French Patent No. 792,353, to Proquitte et al. These nipple covers include openings along their outer surface that permit air to enter the interior of the cover and dry any fluid expelled from the breast. As a result, these covers cannot be used to hold a medicament on a nipple. If they were, the medicament would leak out through the air hole(s) and onto the clothes of the patient. Therefore, the use of these covers would be pointless.

Other types of devices without ventilation holes are also used to cover nipples. One such nipple cover is used to cover the nipples of male long distance runners. Such a cover is disclosed in U.S. Pat. No. 5,743,272, to Kocher, Jr. Unlike the above-discussed covers for lactating nipples, the male nipple covers do not include ventilation openings. Instead, these covers have large, flat outer end surfaces. Additionally, these covers are not laterally or longitudinally flexible. As a result, they do not collapse around the nipple and conform to its shape. Therefore, others will readily notice these nipple covers when worn. This is not acceptable for women who need to wear a medicament containing nipple cover under their clothing during work or other activities in order to prepare their nipples for an examination or procedure such as ductal lavage. These nipple covers will be conspicuous and possibly embarrass the person using them because they can be easily seen under clothing when worn.

SUMMARY

One aspect of the present invention relates to a covering member for a protruding portion of a patient's body. This cover is flexible and collapsible so that it conforms to the shape of the encased portion of the body. This prevents the cover from being noticed while it is worn under clothing. The cover can contain a medicament or agent for treating a portion of the body before and/or after an examination or procedure. When the cover is used to apply a topical anesthetic to a portion of the body for a recommended period of time prior to the procedure or examination commencing, the amount of discomfort experienced by the patient can be significantly reduced compared to the amount experienced by the patient who has the anesthetic applied for just a few moments before the procedure begins. Alternatively, the cover can be used to hold a medicament or agent on the intended portion of the body in order to heal a wound or cure a condition such as a skin rash or the like.

One embodiment includes a cover for a protruding portion of a mammalian body. This cover comprises first and second flexible members. The first member includes a securing portion, at least one sidewall and at least one end wall. The sidewall and end wall form a continuous, uninterrupted well for receiving and covering the protruding body portion. The second flexible member has a first surface for attaching to the securing portion of the first member and a second surface for securing to the body so that the second surface does not move relative to the body.

Another embodiment includes a flexible nipple covering apparatus for enclosing a mammalian nipple. The covering apparatus comprises an anchoring member for securing to a portion of a body carrying the nipple. The cover also includes an uninterrupted nipple receiving well that has at least one sidewall and at least one end wall. The well is secured to the anchoring member in order to form a sealed enclosure about the nipple when the anchoring member is fixed to the body. As a result, the anchoring member and body are free of relative movement.

A further embodiment includes a flexible apparatus for covering and isolating a nipple of a mammalian body. The apparatus comprises a base for positioning proximate an areola and an internal well for receiving the nipple. The well includes at least one sidewall and at least one end wall at an opposite end of the apparatus from the base. The well, the base and the end wall form a continuous, uninterrupted nipple enclosure for holding an agent on the nipple.

The present invention also includes a method of preparing a portion of a body for a medical procedure. The method includes the steps of positioning a flexible covering apparatus including a well and an anchoring member over the body portion and locating the body portion so that it extends within the well. The method also includes the steps of fixing the covering apparatus to the body around the covered body portion so that a seal is formed between the anchoring member and the body and applying an agent to the body portion.

DETAILED DESCRIPTION

Figure 1:
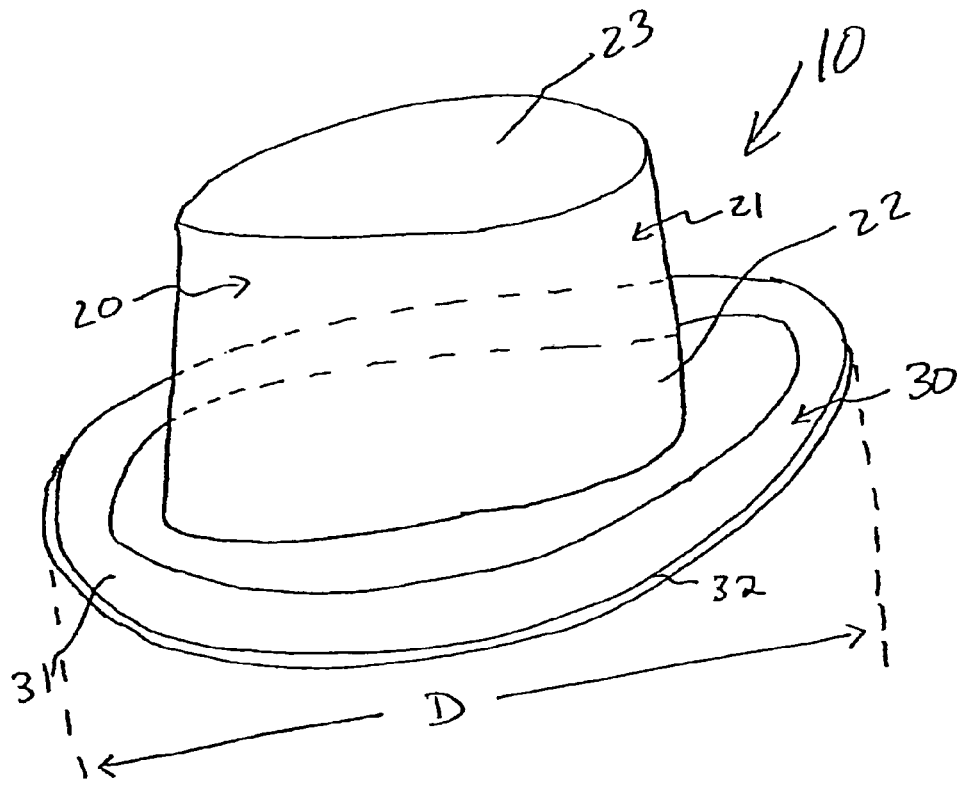
FIG. 1 is a perspective view of a cover for a protruding body portion according to the present invention.
Figure 2:
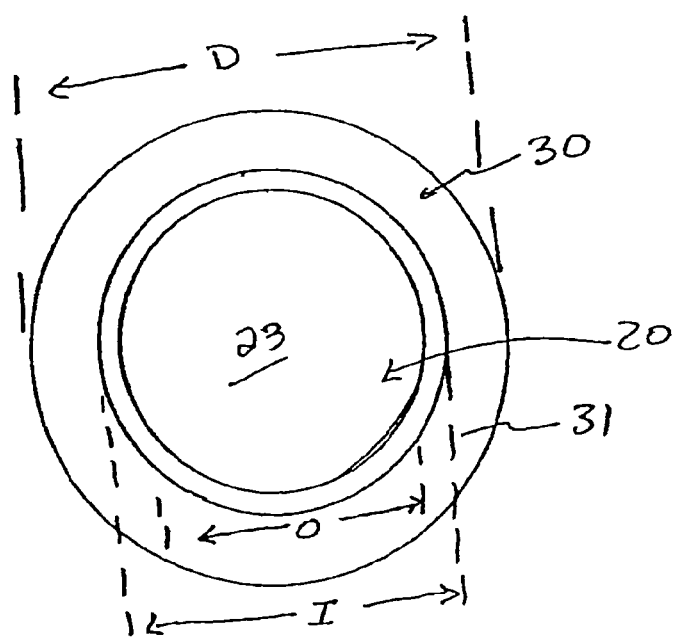
FIG. 2 is a top view of the cover illustrated in FIG. 1.

The present invention relates to a flexible cover 10 for enclosing a protruding body portion and effectively isolating the body portion from its surrounding environment as shown in FIG. 1. The cover 10 can be applied to the body before or after a medical procedure is performed. In one embodiment, the cover 10 is applied prior to a procedure being conducted in order to prepare the body portion 1 for the procedure. In another embodiment, the cover 10 can be used to enclose a protruding portion of the body 1 after a procedure has been performed in order to isolate the body portion 1 and prevent infection. With either embodiment, the cover 10 can hold a desired amount of an effective topical agent 100 on the body portion 1 and prevent the agent 100 from leaking to other parts of the patient's body or his/her clothes. The cover 10 can be repeatedly used as an applicator for initial or supplemental amounts of the agent 100. Alternatively, the cover 10 can be disposed after the first application of the agent 100.

The agent 100 can be any type of topical agent used on the body. For example, the agent 100 can be, but is not limited to, a topical anesthetic capable of anesthetizing a region of a patient's body portion in preparation for a diagnostic examination or another medical procedure. Additionally, the agent discussed herein could include any of the agents disclosed and defined in U.S. Provisional Patent application No. 60/252,090, to Hung and Patel, which was filed on Nov. 21, 2000, and entitled "Preparation for Breast Duct Fluid Collection." This provisional application is hereby fully incorporated by reference. Additional agents that are customarily used on the body after an operation can also be retained and/or applied on the body portion 1 by the cover 10.

As used herein, the term procedure can include any of the medical procedures discussed above or any additional procedures that are known to medical practitioners. For ease of explanation, the cover 10 will be described as it is used to prepare a breast nipple for a diagnostic examination such as ductal lavage. Ductal lavage includes the introduction of a fluid into a mammalian breast duct and the retrieval of a composition from within the duct via a lumen that extends through the nipple and into the duct. U.S. patent application Ser. No. 09/473,510, to Hung et al., which is hereby incorporated by reference, provides a more detailed description of ductal lavage. While, the present invention is being described with respect to ductal lavage, its use is not limited to this procedure. For example, as discussed above, it may be used to cover and retain a medicament on other portions of a body including a pediatric penis and a nose. The cover 10 can also be applied over one or more fingers or toes.

FIG. 1 illustrates a first embodiment of the cover 10 for positioning over a protruding body portion. While this embodiment of the cover 10 and the others disclosed below can be used to cover many different body parts, such as those discussed above, for clarity, the cover 10 will only be discussed as it is used to cover a nipple 110, shown in FIG. 4, in order to prepare the nipple 110 for a medical procedure. The preparation includes the steps of (1) applying an anesthetizing agent to the nipple 110, (2) positioning the cover 10 over the nipple 110 and (3) forming a seal between the cover 10 and the patient's body. The formed seal prevents the agent from leaking out of the cover 10 and onto other parts of the patient, including her clothes. According to the present invention, the agent can be applied directly to the nipple 110, applied only within the cover 10 or a combination of both.

The cover 10 then encloses the nipple 110 for a predetermined period of time that is sufficient to prepare it for the intended procedure. The cover 10 and agent can be securely positioned over the nipple 110 for about two minutes to about forty-eight hours prior to the procedure. In a preferred embodiment, the cover 10 and agent are securely positioned over the nipple 110 for about one hour to about ten hours prior to the procedure. In another preferred embodiment, the cover 10 and agent are securely positioned over the nipple for about two hours to about four hours prior to the procedure.

The cover 10 is a unitary, continuous uninterrupted enclosure that isolates the nipple 110 from its surrounding environment. As shown in FIG. 1, the cover 10 includes a body portion covering chimney 20 and a base 30 that is secured to the patient after the cover 10 has been positioned over the nipple so that a seal is formed between the patient and the cover 10. As used herein, the term "chimney" refers to an elongated portion of the cover 10 that includes an internal receiving well and that extends longitudinally away from the base 30 in the same direction that the nipple 110 protrudes from the body. The shape and size of the chimney 20 and the base 30 will depend on the portion of the body they are intended to cover. For example, the cover 10 for a nipple may have different dimensions than a cover 10 for a toe.

Figure 3:
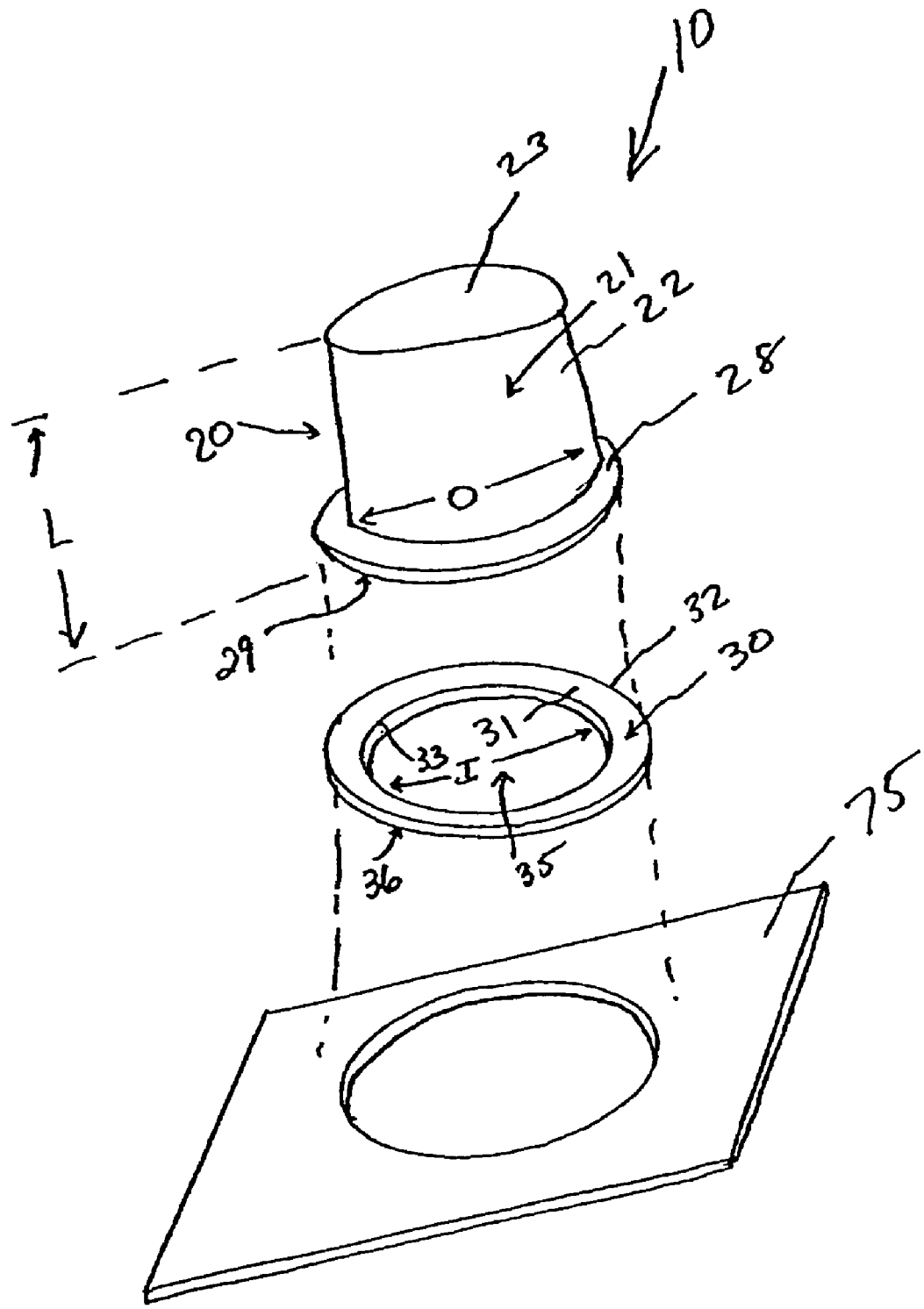
FIG. 3 is an exploded perspective view of the cover.
Figure 5:
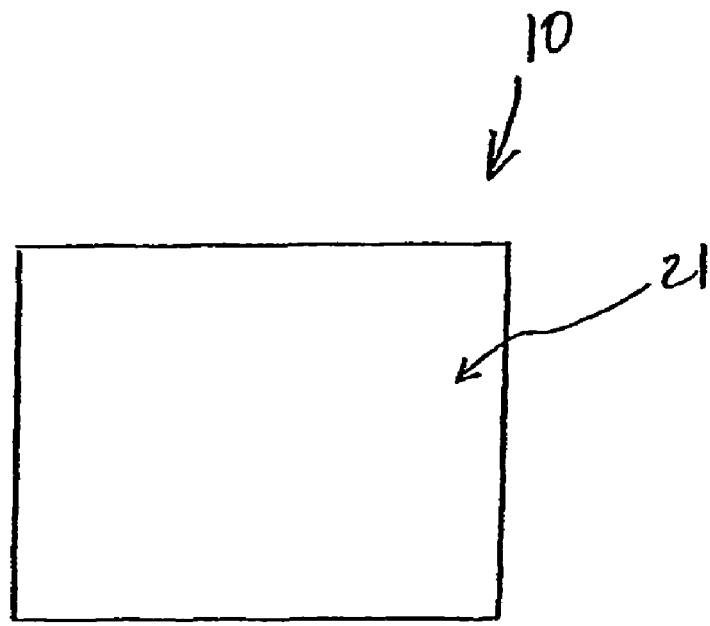
FIG. 5 illustrates the cross section of an alternative embodiment of the cover according to the present invention.
Figure 6:
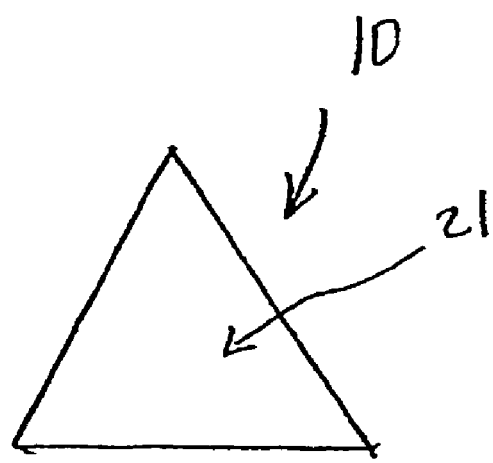
FIG. 6 illustrates the cross section of a third embodiment of the cover according to the present invention.

As shown in FIG. 3, the chimney 20 includes an agent and a nipple receiving well 21. The chimney 20 also includes portion that forms a securing ring 28 having a lower surface 29 for attaching to the base 30 as discussed below. The well 21 is defined by at least one sidewall 22 and a distal end wall 23. The number of sidewalls 22 will vary with the shape of the well 21. For example, a well 21 that has a circular, substantially circular or elliptical cross section may have only one sidewall 22. However, a well 21 with a triangular, square, rectangular, diamond, or other known polygonal cross section will include more than one sidewall 22 as shown in FIGS. 5 and 6. The distal end wall 23 forms a continuous barrier at one end of the sidewalls 22 of the well 21. The securing ring 28 and end wall 23 are integrally formed with the sidewall(s) 22 so that the sidewall(s) 22, end wall 23 and securing ring 28 form a continuous, uninterrupted, flexible enclosure around the nipple 110. In a preferred embodiment, sidewall(s), end wall 23 and securing ring 28 are formed from the same piece of material. Alternatively, they can be formed of separate pieces of material and secured together. Well known securing techniques such as RF welding can be used. The end wall 23 can be flat, rounded or stepped in between the outer edge(s) 26 of the sidewall(s) 22.

In an embodiment, the sidewall(s) 22, end wall 23 and securing ring 28 are formed of a flexible, easily manipulated material that can be stretched into any desired shape. The material is preferably biocompatible and hypoallergenic. The material can also be resilient. A resilient material will permit the cover 10 to stretch and conform to the shape of the nipple 110. In another embodiment, the material holds its shape after it experiences elastic deformation. For example, in one embodiment, the flexible, easily manipulated material includes a linear low density polyethylene (LLDPE). Other known flexible, stretchable and/or elastic materials may be used to form the chimney 20. Examples of these well-known materials include, but are not limited to, other types of polyethylene, plastics, thermoset polymers, thermoforming polymers, paper, TYVEK®, webbed materials, composites, and polyesters.

In an embodiment, the flexible material used for at least the sidewall(s) 22 and the end wall 23 is partially transparent so that the nipple 110 can be seen through the cover 10. In another embodiment, the material is completely transparent so that the patient, attendant and/or physician can easily view the nipple 110 and determine the extent of its preparation or healing without having to remove the cover 10. The transparent aspect of the material permits someone to determine if additional amounts of the agent need to be applied to the nipple 110 without having to break the seal between the base 30 and the patient. The securing ring 28 does not need to be formed of a transparent material. However, if it is formed from the same sheet of material as the transparent chimney 20 than it may be transparent. Alternatively, the securing ring 28 may also be transparent if the base 30 is at least partially transparent. In this alternative embodiment, the cover 10 could be easily and accurately positioned on a particular portion of the body.

The chimney 20 is easily deformable (elastic) under pressure. As a result, it will collapse around and substantially conform to the shape of the nipple 110 as the cover 10 is being applied to the body. Typically, the patient or attendant applying the cover 10 will apply pressure to the chimney 20 as the cover 10 is applied so that air is expelled from the well 21 and the sidewall(s) 22 and end wall 23 conform to the shape of the nipple 110. Since the chimney is able to collapse and substantially conform to the shape of the nipple 110, the cover 10 will not be visible when it is worn under a patient's clothing. This is especially important for a woman who may feel self conscious and uncomfortable when a strange shape protrudes from underneath her blouse. The cover 10 illustrated in the figures allows a patient to discreetly wear a cover 10 over her nipple 110. This can encourage the use of the cover 10 in the future. Additionally, as the chimney 20 collapses, any agent within the well 21 will be forced into contact with the nipple 110.

As shown in FIG. 1, the portion of the chimney 20 that forms the securing ring 28 is secured to an upper surface of the base 30 by adhesives. In another embodiment, the securing ring 28 has a cohesive on its lower surface 29. The cohesive cooperates with a cohesive carried by the upper surface of the base 30 that is already secured onto the areola or another portion of the body surrounding the nipple 110. The use of cohesives permits easy removal of the chimney 20. The cohesives also allow for the chimney 20 to be repeatedly removed without the patient feeling any uncomfortable tugs on her areola. Additionally, the cohesives will not stick to the person removing or replacing the chimney 20 when the base 30 is left on the patient for an extended period of time.

The base 30 includes a main body ring 31 that makes the cover 10 easy to handle and position over the protruding nipple 110. The ring 31 extends in a direction away from the body (thickness) between about 0.0156 inch and 0.25 inch. In one embodiment, the ring has a thickness of about 0.0625 inch. In another embodiment, the ring 31 is about 0.03125 inch thick.

In one embodiment, the ring 31 is formed of biocompatible, hypoallergenic cross-linked polyethylene foam that is available from Scapa Medical® having a tensile strength of at least about 160 psi and an elongation of at least about 290%. Other materials that can be used for ring 31 include, but are not limited to, other polyethylene foams, polyesters, papers, polyethylene liners, plastics and polypropylenes.

Figure 4:
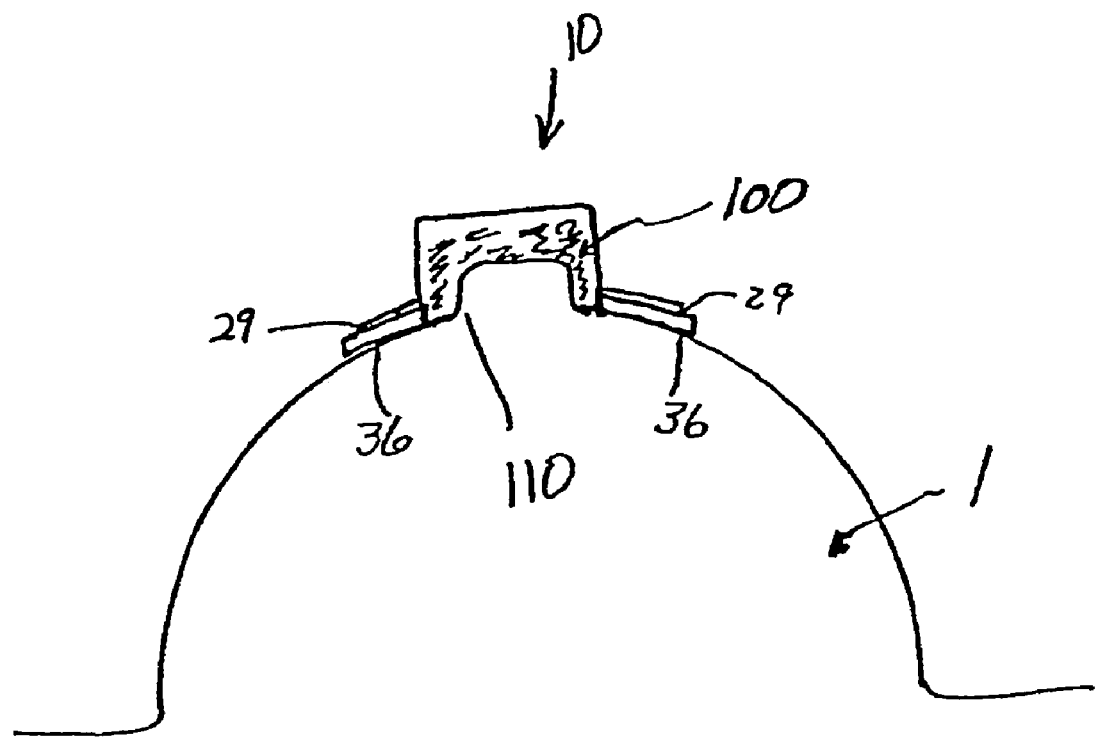
FIG. 4 is schematic view of the cover illustrated in FIG. 1 secured over a nipple.

The ring 31 is semi-rigid. It is stiff enough that a person can firmly hold onto it an easily manipulate the cover 10 without adhesive carrying portions of the cover 10 becoming secured to each other. The ring 31 can be stiff enough to permit one-handed application of the cover 10. Yet, the ring 31 is flexible enough to conform to the shape of the person's body that surrounds the nipple 110. The ring 31 is defined by an outer edge 32 and an inner edge 33. As shown in FIG. 4, the inner edge 33 extends around the base of the nipple 110 when the base 30 is secured to the patient as discussed below. The inner edge 33 defines an opening 35 that forms a nipple receiving entrance to the well 21. When the cover 10 is positioned on the patient, the nipple 110 will be received in the opening 35 and extend into the well 21.

The base 30 is shown as being circular in shape for ease of explanation. However, the base 30 can have any shape that permits it to securely hold an agent carrying chimney 20 over the nipple 110. Also, while the opening 35 is shown to match the shape of the opening to the well 21, the opening 35 can have any shape that cooperates with one of the above listed cross sections of the chimney 20 to receive the nipple 110. Additionally, the shape of the outer edge 32 of the base 30 does not need to match the shape of the inner edge 33. Instead, as mentioned above, the outer edge 32 can have any shape that permits the cover 10 to be securely positioned on the patient and over the nipple 110.

The ring 31 also has a lower surface 36 for contacting and being secured to the patient's body. When the cover 10 is positioned over the nipple 110, the lower surface 36 is sized so that it covers a portion of the epidermis and/or the areola around the nipple 110. An adhesive or other well-known securing element covers the lower surface 36 so that is can be securely positioned on the patient. The adhesive can be any known, medically approved skin adhesive, such as those approved by 3M®. In one embodiment, the adhesive is a synthetic rubber based medical approved skin adhesive (I-832) available with the ring 31 from Scapa Medical®. When an adhesive is used on the lower surface 36, a removable release sheet 75 extends over the lower surface 36 to prevent the cover 10 from erroneously adhering to the body portion. In one embodiment, the release sheet 75 includes a polyethylene coated paper having a silicone release coating on one side.

The adhesive can secure the lower surface 36 to the patient's body for either a short or an extended period of time. The surface 36 can be secured to the patient for between about two minutes and about forty-eight hours prior to (and/or after) the procedure. In one embodiment, the surface 36 is secured to the patient for about one hour to about ten hours. In another embodiment, the surface is secured to the patient for about two hours to about four hours.

In one embodiment, the chimney 20 is removed and the ring 31 stays secured on the patient throughout the procedure. In this embodiment, the ring 31 acts as a location to place or affix other items such as tubes and/or tethers etc. The adhered ring 31 may remain or be replaced with a post procedure cover 10, for example containing an antibiotic and/or a wound healer, etc.

As can be clearly understood, during the application of the cover 10, the release sheet 75 is removed immediately before the cover 10 is applied over the nipple 110 and secured to the body. Alternatively, the release sheet 75 could include two separate pieces. In this embodiment, one piece is removed after the cover 10 has been positioned over the nipple 110. Then, the exposed adhesive can be applied against the body so that a partial seal is formed between the cover and the body. Next, the second release sheet will be removed and the base 30 pressed against the body. This will close the seal between the body and the cover 10. The seal will prevent any of an applied agent from leaking out of the cover.

In an alternative embodiment, the lower surface 36 can be free of an adhesive. If the lower surface 36 does not include an adhesive, strips of adhesive carrying tape could be extended across the base 30 to secure the cover 10 to the patient. In another embodiment, the cover 10 could have a cohesive on the lower surface 36 that will cooperate with a cohesive carried by an outer surface of a ring that is already secured onto the areola or another portion of the body surrounding the nipple 110. The use of cohesives allows the cover 10 to be positioned on the body without the chance of the lower surface 36 becoming erroneously secured to the attendant applying the cover 10 or on another portion of the patient's body. Additionally, the cohesives permit the cover 10 to be removed without the patient feeling the discomfort of having an adhesively secured cover being ripped off their sensitive areola. In this alternative embodiment, the body contacting ring is secured to the patient using an adhesive or other well-known securing arrangement.

No matter the manner in which the cover 10 is secured to the patient's body, the lower surface 36 must have enough surface area that it forms an effective seal with the patient's body. The seal must be strong enough to prevent the cover 10 from separating from the body. The size of the lower surface 36 will vary depending on a number of factors. These factors include at least the following: the length of the chimney 21, the amount of pressure that will be normally applied to the chimney 21 in order to form it to the shape of the nipple 110 and the weight of the amount of the agent that will be applied to the patient and carried by the cover 10 when the chimney is filled with the agent. The surface area of the lower surface 36 is larger for the covers 10 having longer chimneys 21 and/or the covers 10 having large wells 21 intended to carry large amounts of the agent. No matter the length of the well 21, the lower surface 36 must have enough surface area that it forms an effective seal with the patient's body. The seal must be strong enough to prevent the cover 10 from separating from the body.

As seen in the figures, the chimney 20 has a length L of about 0.001 inch to about 3.0 inches. In one embodiment, the length L is about 0.25 inch to about 2.0 inches. In another embodiment, the preferred length L is about 0.63 inch. The diameter D of the base 30 and securing ring 28 is about 0.5 inch to about 3.0 inches. In one embodiment, a preferred diameter D is about 2.0 inches. The diameter I of the opening 35 is about 0.25 inch to about 2.5 inches, with a preferred diameter being about 1.0 inch. The diameter O of the well 21 at the securing ring is about 0.5 inch to about 2.0 inches. A preferred diameter O is about 1.0 inch. The diameter of the end wall 23 can be the same as diameter O or it can be slightly smaller so that the chimney 20 has a tapered profile. The term diameter can refer to corresponding widths for those embodiments that do not have circular cross sections.

The above-discussed dimensions are exemplary. Each dimension of the cover 10 can be individually set to match the size of the patient's nipple. For example, it is possible to make the diameter O slightly smaller than the diameter of the patient's nipple 110 so that the chimney forms a secure fit with the base of the nipple 110. The diameter of the opening 35 does not need to be a function of the length of the chimney 20. Instead, the size of the opening 35 is chosen based on the diameter of the nipple 110 that it will cover.

The cover 10 can be manufactured using any known method for forming a well in a sheet of flexible material. One method of forming the cover 10 according to the present invention includes the stop of cold working the material until the well 21 is formed. The step of cold working the material includes advancing a blunt object, such as a flat or rounded head punch, into the material until a well having sufficient depth to cover the nipple 110 and hold the agent is achieved. Another known way of forming the cover 10 includes thermoforming it using the method currently used to form bubble wrap. Additional forming methods include injection molding, compression molding and transfer molding.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A flexible cover configured to be selectively positioned over a nipple of a patient's breast, comprising:
    a base configured to be secured to a portion of the breast surrounding the nipple;
    a well secured to the base, said well comprising at least one sidewall and an end wall, said end wall forming a continuous barrier along one end of said at least one sidewall;
    wherein the side wall and the end wall of the well are integrally formed;
    wherein the well comprises a polymeric material that is generally flexible and resilient, said polymeric material being biocompatible and hypoallergenic;
    wherein the well is configured to receive the nipple when the cover is positioned on the breast;
    wherein the well is configured to at least partially contact the nipple when the cover is applied to the breast; and
    an adhesive located along a bottom surface of the base, said adhesive configured to secure the cover to the breast, wherein said adhesive comprises a medically approved skin adhesive; and
    wherein the cover creates a seal with the breast so that fluids within the well are maintained within said well while the cover is secured to the breast.

2. The flexible cover of claim 1, further comprising a release sheet, said release sheet configured to releasably secure to the lower surface of the base.

3. The flexible cover of claim 1, wherein the well comprises a generally circular or elliptical cross-sectional shape.

4. The flexible cover of claim 1, wherein the base and the well are integrally formed.

5. The flexible cover of claim 1, wherein the base is semi-rigid.

6. The flexible cover of claim 1, wherein the well is configured to substantially conform to a shape of the nipple as the cover is applied to the breast.

7. The flexible cover of claim 1, wherein the well is configured to reduce leakage of any ductal fluid collected from the nipple.

8. The flexible cover of claim 1, wherein the well comprises a length between about 0.0001 and 3 inches.

9. The flexible cover of claim 1, wherein the well comprises a length between about 0.5 to 3 inches.

10. A cover configured to be selectively positioned over a nipple of a patient's breast, comprising:
    a base configured to be secured to a portion of the breast surrounding the nipple;
    a well secured to the base, said well comprising at least one sidewall and an end wall, said end wall forming a continuous barrier along one end of said at least one sidewall;
    wherein the well comprises a polymeric material that is generally flexible and resilient, said polymeric material being biocompatible and hypoallergenic;
    wherein the well is configured to receive the nipple when the cover is positioned on the breast;
    wherein the well comprises a length between about 0.0001 and 3 inches;
    wherein the well is configured to contact the nipple and reduce leakage of any ductal fluid collected from the nipple;
    wherein the well is configured to at least partially conform to a shape of the nipple when the cover is applied to the breast; and
    an adhesive located along a bottom surface of the base, said adhesive configured to secure the cover to the breast, wherein said adhesive comprises a medically approved skin adhesive; and
    wherein the cover creates a seal with the breast so that any fluids within the well are maintained within said well while the cover is secured to the breast.

11. The cover of claim 10, further comprising a release sheet, said release sheet configured to releasably secure to the lower surface of the base.

12. The cover of claim 10, wherein the well comprises a generally circular or elliptical cross-sectional shape.

13. The cover of claim 10, wherein the base and the nipple receiving well are integrally formed.

14. The cover of claim 13, wherein the base, the sidewall and the endwall are integrally formed from a unitary piece of material.

15. The cover of claim 10, wherein the well comprises a length between about 0.5 to 3 inches.

16. The cover of claim 10, wherein the well is configured to substantially conform to a shape of the nipple as the cover is applied to the breast.

17. The cover of claim 10, wherein the base is semi-rigid.

* * * * *